Figure 1:
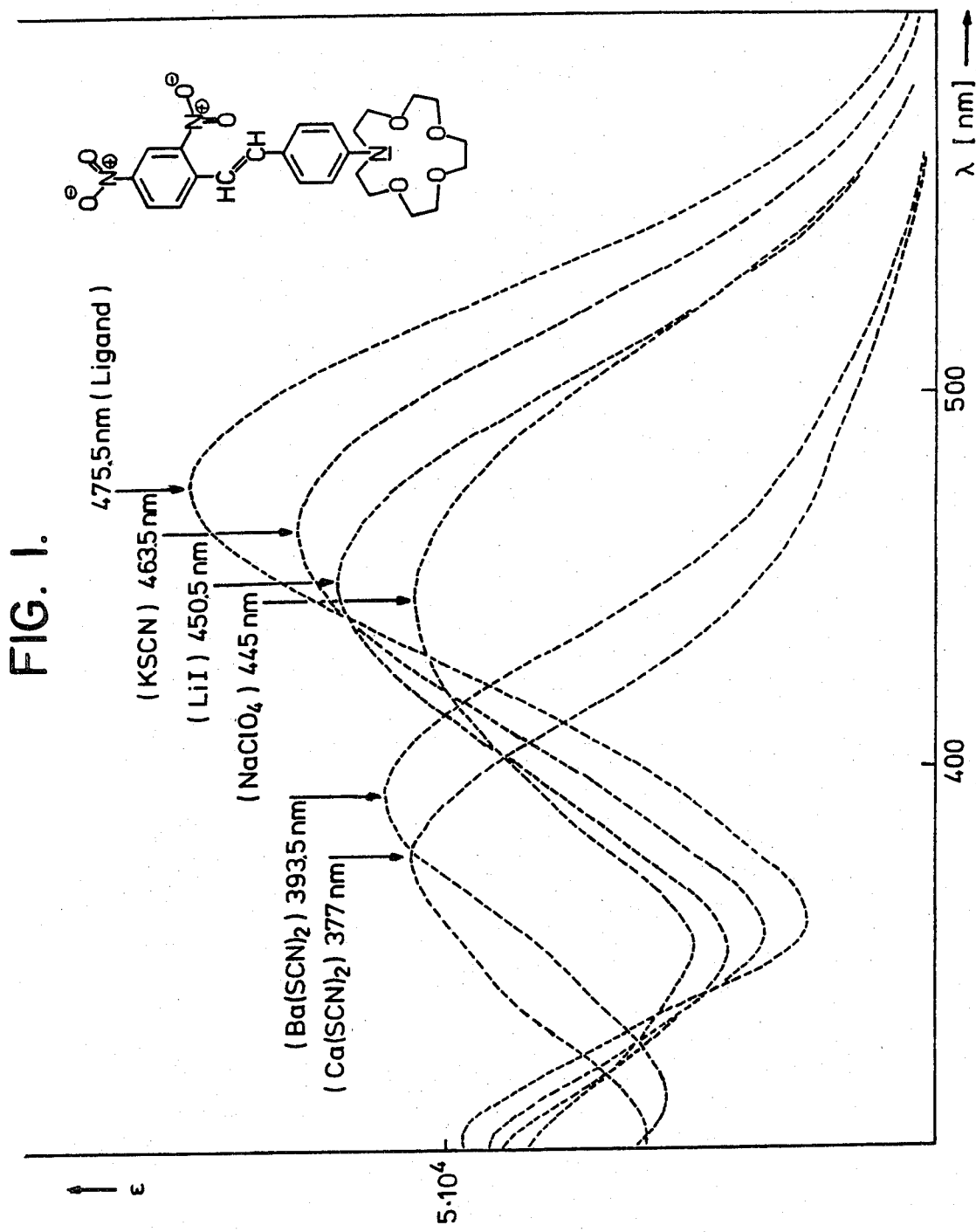

United States Patent [19]

Vögtle et al.

[11] 4,367,072
[45] Jan. 4, 1983

[54] LIGANDS ASSAYED BY HOST MOLECULES INCLUDING CYCLOPHANES, CROWN ETHERS, CRYPSTANDS AND PODANDS

[75] Inventors: Friedrich Vögtle, St. Augustin; Johannes P. Dix, Bonn-Beuel; Dieter Jaworek, Weilheim, all of Fed. Rep. of Germany

[73] Assignee: Boehringer Mannheim GmbH, Mannheim-Waldhof, Fed. Rep. of Germany

[21] Appl. No.: 78,738

[22] Filed: Sep. 25, 1979

[30] Foreign Application Priority Data

Oct. 2, 1978 [DE] Fed. Rep. of Germany ....... 2842862

[51] Int. Cl.$^3$ ...................... G01N 31/22; G01N 33/52
[52] U.S. Cl. .................... 436/501; 436/805; 436/808; 436/815
[58] Field of Search ............. 23/230 R, 230 B; 424/8, 424/12

[56] References Cited

U.S. PATENT DOCUMENTS

| | | | |
|---|---|---|---|
| 3,789,116 | 1/1974 | Kay | 424/8 |
| 3,950,135 | 4/1976 | Whitesides | 23/230 R |
| 3,992,149 | 11/1976 | Wang | 23/230 R |
| 4,005,983 | 2/1977 | Dahms | 23/230 R |
| 4,013,414 | 3/1977 | Lavalle | 23/230 R |
| 4,099,918 | 7/1978 | Keand | 23/230 R |

OTHER PUBLICATIONS

J. Grandjean et al., Angew. Chem., Int. Ed. Engl., 17(11), 856–857 (1978).
J. Peter Dix et al., Agew. Chem., Int. Ed. Engl., 17(11), 857–859 (1978).
Chemical Abstracts, 88:145429y (1978).

*Primary Examiner*—Sidney Marantz
*Attorney, Agent, or Firm*—Felfe & Lynch

[57] ABSTRACT

Method for the determination of a component in a liquid which component is selected from ions, polar substances lipophilic substances, which comprises contacting a liquid sample containing said component with, and allowing same to act upon, a complex ligand or host molecule which is selective toward the component, said complex ligand or host molecule being bonded to a chromophore material, and measuring the change of extinction or the wavelength displacement of the resulting mixture as a measure of the initial content of said component; corresponding reagent test kits are also provided. The complex ligands or host molecules include cyclodextrins, cyclophanes, crown ethers, cryptands, podands, valinomycin, gramacidin and nonactin.

33 Claims, 6 Drawing Figures

LIGANDS ASSAYED BY HOST MOLECULES INCLUDING CYCLOPHANES, CROWN ETHERS, CRYPSTANDS AND PODANDS

This invention relates to the analysis of fluids, particularly biological fluids. More specifically, the invention is concerned with a method and reagent for the determination of ions and of polar and lipophilic substances in fluids.

The qualitative and quantitative determination of individual ions in physiological fluids is of great importance for diagnosis, therapy and monitoring in the field of medicine, as well as in the control of chemical and microbiological processes. In clinical diagnosis, chemical processes have hitherto been described with dyestuffs, as well as spectrophotometric processes and also methods using ion-seclective electrodes.

In the case of flame emission analysis (flame photometry), the intensity of the light emitted by excited atoms is measured photoelectrically at the wavelength corresponding to the element.

In contradistinction thereto atomic absorption spectroscopy measures nonexcited atoms of atom absorption spectroscopy, nonexcited atoms are used, the concentration of which lies some factors of ten higher. The advantages of atomic absorption methods are the greater sensitivity, as well as the absence of spectral interference. Disadvantages in comparison with emission analysis include the relatively high expense of the apparatus, the very large sample volumes needed (2 ml.), the low sample frequency, as well as the separate and sequential determination of both parameters. Although this process is regarded as being a reference method for the determination of sodium and potassium, nevertheless, it remains limited to medical-scientific laboratories.

For the simple and rapid determination also of ion concentrations or activities in aqueous solutions, ion-sensitive electrodes (ISE) can be used which, in comparison with the spectrophotometric process, require less expensive apparatus. Disadvantages of these ion-selective electrodes include the relatively long and, in some cases, varying response time of the electrodes and the blocking up of the electrode sensors by high and low molecular weight substances present in the sample so that these only have relatively low stabilities.

The present invention provides a rapid and dependable process which can be carried out in liquid tests and by way of solid test strips, for the determination of ions and of polar and/or lipophilic substances in fluids and especially in biological fluids, such as blood serum.

The method of the invention comprises contacting the substances to be determined with a complex ligand or host molecule which is selective towards the ion or the polar and/or lipophilic substances to be determined, and allowing the ion or substance to act on said ligand or host molecule; the complex ligand or host molecule is attached by a direct covalent bond or heteropolar bond or hydrogen bridge or hydrophobic bond to a chromophore or material containing a chromophore complex; the change of extinction or wavelength displacement is then measured as a measure of the initial substance to be determined.

The invention also provides a reagent for the determination of ions or of polar and/or lipophilic substances in liquids, which contains one or more complex ligands or selective host molecules of the same or different type which are selective towards the ions to be determined or to the polar and/or lipophilic substances, these being linked by direct covalent, heteropolar or hydrophobic bonds with one or more chromophores of the same or different type, or contains the chromophores in the form of an inclusion complex.

Furthermore, the present invention provides a test kit comprising at least one of the above-mentioned reagents.

The selective complex ligand or selective host molecule used can be a cyclic or acyclic medio- or macromolecular compound which, with regard to the ion to be detected or with regard to the polar and/or lipophilic substance to be detected is already present as a complex former or as a host molecule or, in the presence thereof, assumes the structure necessary for the complex formation or adduct formation in the form of the host-guest exchange action. The polar ranges are thereby extended towards this in the presence of the ion. The ring size and structure of the host molecule provide the selectivity in dependence upon the effective diameter or the specific polar or hydrophobic character of the complexing guest ion or guest molecule. In the case of complex formation, the ligand frequently changes its conformation thereby influencing complex formation and complex dissociation. Thus, as complex ligands or host molecules there can be used compounds of the oligoether, polyether, oligo ester, polyester, oligoamide and polyamide types. Examples of suitable compounds include crown ethers, cryptands, podands and derivatives thereof, as well as cyclic peptides and peptides which, in the presence of the ion to be determined or of the polar substance, assume the secondary, tertiary or quaternary structure necessary for the complex formation. Furthermore, there can be used tetrahydrofuran-containing, esterbonded macrolides and analogous compounds which regulate or can regulate the transport in biological systems. There can also be used pure hydrocarbon structures, such as lipophilic host molecules ("lipophilic hollow spaces"), such as cyclodextrins and cyclophanes. Combinations of the above functions are also possible.

The derivatives of the complex ligands or host molecules can possess bridges or chains which can contain oligo- or polyethylene glycol groupings or other hetero atom-containing groupings.

The covalent, heteropolar or hydrophobically-bound chromophore is a dyestuff or fluorescent dyestuff or a chromogen, the absorption spectrum of which changes due to a reciprocal action, such as charge displacement and disturbance of the mesomerism either in the base and/or excited state by the guest particles, such as polar ions or lipophilic guest molecules. The dyestuffs used can be, for example, those of the polyene, meriquinoid, quinone, azo (such as methyl orange and methyl red), pyrrole, merocyanine, indigo, indophenol, stilbene, azomethine, anthraquinone, naphthoquinone, cyanine, phthalein, polymethine and alizarine types.

The chromophore contained in the inclusion complex or in the host molecule can be an acid dyestuff or a salt thereof, for example, a lithium, sodium, potassium, ammonium, calcium, alkylammonium or magnesium salt. The dyestuff preferably contains a carboxylate, sulphonate, phenolate or thiophenolate grouping. The ions to be detected can be cations or anions and are especially alkali metal ions (for example lithium, sodium or potassium ions), ammonium ions, alkaline earth metal ions (for example magnesium or calcium ions) or other metal ions, such as heavy metal ions (for example iron, zinc, copper, cobalt, nickel, molybdenum and chromium ions). In particular, there can also be detected organic ions, for example oligoalkylammonium ions, phosphonium ions, guanidine ions and choline ions. Anions which can be detected include, in particular, chloride, bromide, iodide, sulphate, nitrate, nitrite, phosphate, diphosphate, triphosphate, hydrogen phosphate and hydrogen carbonate ions. As examples of neutral polar substances, there can be mentioned neutral guest particles, for example, urea, thiourea, guanine, guanidine, uric acid, choline, creatinine, amino acids and sugars, and as typical lipophilic guest molecules, steroids, for example cholesterol, and lipids, such as triglycerides and lecithins.

The cation and anion concentration, as well as the concentrations of neutral guest particles can, in this simple manner, be recognized qualitatively and quantitatively by color effects, i.e. photometrically.

The selectivity can refer not only to a single, quite definite ion or substance to be detected but also to a group of ions or a group of substances. For this purpose, use can be made, for example, of chromophores, such as dyestuffs with several identical or different complex ligands or host molecules, such as crown ethers of different hollow space size, such as are illustrated in the following formula:-

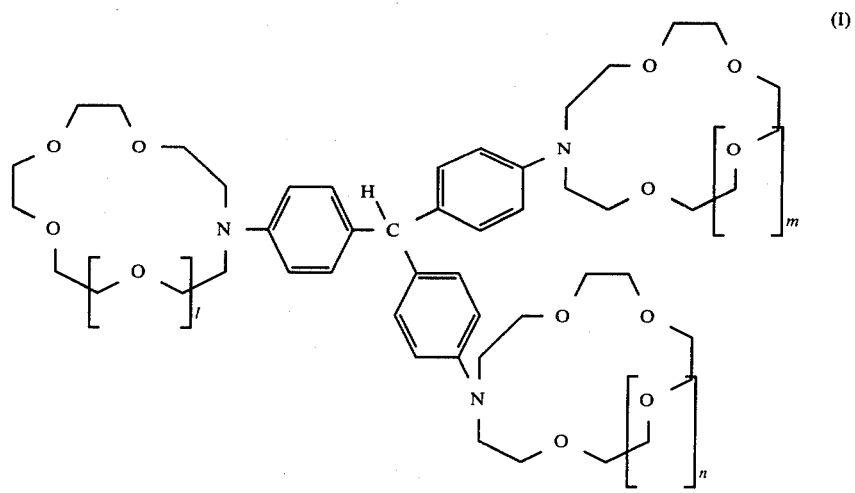

wherein l, m and n preferably mean 0, 1, 2, 3 or 4.

Furthermore, there can be attached to a complex ligand or a host molecule, such as the crown ether structure, one or more identical or different chromophores, such as dyestuffs. The color change can, for example, depend upon the following mechanism:

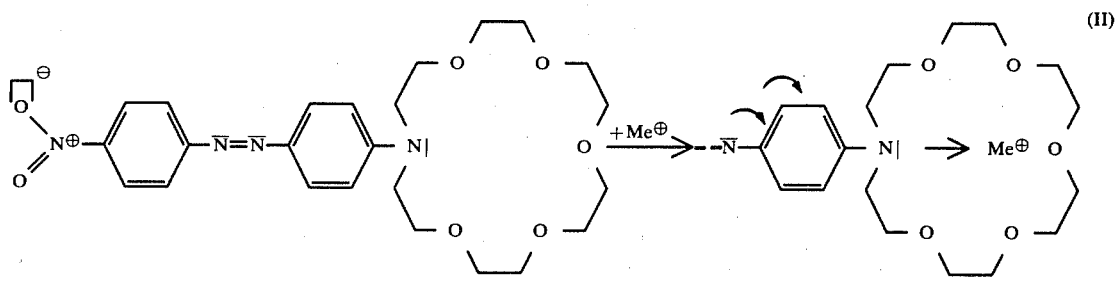

wherein Me⊕ can be, for example, an alkali metal, alkaline earth metal, ammonium or heavy metal ion, and wherein the mesomeric system is based upon the following equation (III), the weight and thus the energy content of which are usually different in the base and excited state:

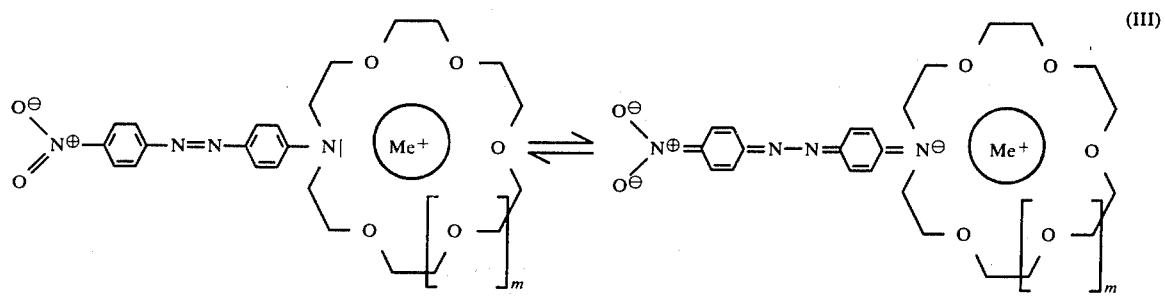

wherein m is 0, 1, 2, 3 or 4.

The crown ether, cryptand and podand chemistry comprises, for example, a large number of methods for linking comparatively large and average rings, as well as bi- and tricyclic systems with —(CH$_2$)$_n$—, aryl- and hetero atom-containing structural elements. Crown ethers, cryptands and podand molecules have the ability of forming stoichiometrical, crystalline complexes, as well as the selective or specific complexing of, for example, alkali metal, alkaline earth metal, ammonium and heavy metal ions, and also of neutral molecules. Numerous experimental results are available regarding the phase transfer behavior of the mentioned compounds.

For the definitions of crown ethers, cryptands and podands, reference is made to the review by F. Vögtle et al. in Kontakte (E. Merck) 1/77, page 11; 2/77, page 16; 3/77, page 36; 2/78, page 16; 3/78, page 32; and 1/79, page 3.

In spite of the extensive investigations, on the one hand in the chemistry of the crown ethers, cryptands and podands, with regard to syntheses and complexings, as well as, on the other hand, with regard to the ion influencing of the color, for example in the case of mordant dyestuffs, complexometric indicators and porphyrin dyestuffs, hitherto nothing has been known regarding the combination of these two fields.

There is a series of publications regarding relevant bridgings in the case of cyclophanes and crown ethers, with the utilization of the dilution principle and template effect. Extensive knowledge is available regarding the synthesis and complexing behavior of cyclic crown ethers and cryptands. In addition, in particular, reactions have been successfully carried out on crown ether systems. Previous experience in this field enables, on the one hand, the synthesis of appropriate crown ethers and cryptand structural units and, on the other hand, the introduction of oligoethylene glycol or other hetero atom-containing bridges.

A series of azo dyestuffs, as well as of di- and triphenylmethane dyestuffs, have been prepared from constructional units of the following general formula (IV), in which R$_1$ is a hydrogen atom and n is 1, 2 or 3, and of general formula (IV'). On these azo dyestuffs, there can be observed, depending upon the ring size, a selective displacement of the visible absorption maximum in a certain direction which is specific for each ion and which frequently involves a change of the molar extinction. The greatest of the spectral changes, such as $\lambda_{max}$, usually brings about the optimum appropriate cation in a particular crown ether ring within one Group of the Mendeleef Periodic System with regard to the radius.

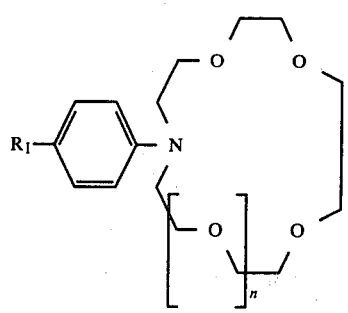

(IV)

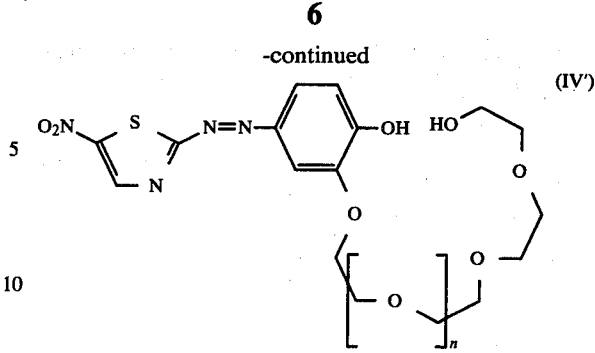

(IV')

Various dyestuffs systems have been provided with crown ether and cryptand units of variable ring size and structure. This hereby also involves the variation in the lipophilic properties or of the hydrophilic properties within the hollow space and on the periphery of the crown ether ring. Both structural elements are to be joined to one another in such a manner that one or more donor hetero atoms of the ligand are simultaneously essential components of the chromophore. A complexed cation attacks a sensitive part of the chromophore more or less intensively and this specifically influences its absorption. This action on the absorbed system depends upon factors such as the size of the ion, its charge or charge density and solvation not only of the dyestuff but also of the cation or anion, as well as the solvent.

The phenylaza-crown ethers of the general formula (IV) type are especially suitable because of their analogy with N,N-dimethylaniline and similar anilines which are often used in dyestuff chemistry. By means of azo coupling, dyestuffs of the general formula (IV) type can be prepared, the non-crowned analogues of which are known as light-fast textile dyestuffs, wherein, for example, n is 1 and R$_1$ is one of the following radicals:

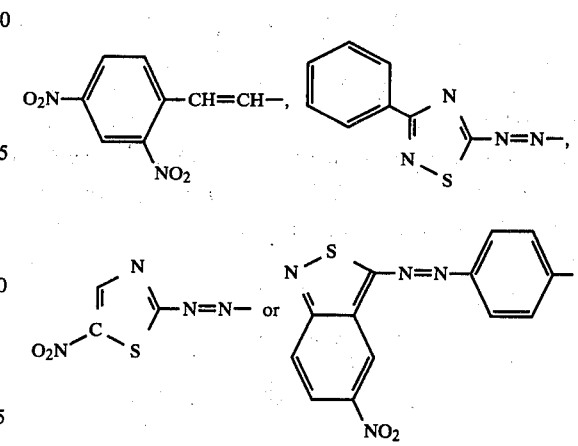

The auxochromic crown ether nitrogen here permits a hypsochromic displacement of the absorption maximum in the case of the exchange reaction with the guest ion since its free electron pair, after complexing has taken place, is not available or is only partly available for mesomery, depending upon the nature of the complexed ion, for example the charge. A further increase of the ion selectivity can be achieved by the partial reinforcement of the crown ether ring, for example in the phenylaza-benzo-crown ethers of the general formula (V) type, in which n is 1, 2 or 3, which can be used, for example, as azo coupling partners and for similar reactions.

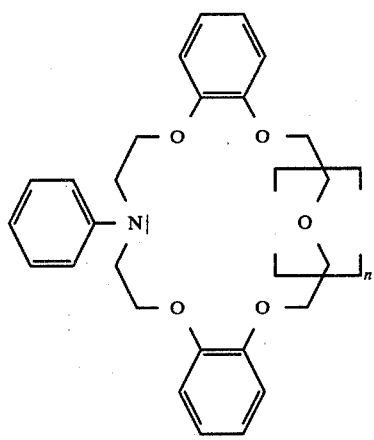

Especially preferred for the practice of the invention are chromophore systems which are readily influenced by a complexed ion, for example, those with a high solvatochromy, such as indophenols of the general formula (IV) type, in which $R_1$ is a radical of the formula:

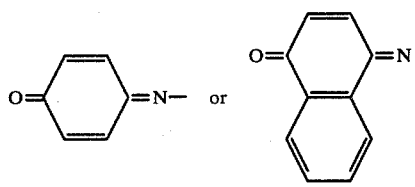

which can be prepared via compounds of general formula (IV), in which $R_1$ is a nitro or primary amino group. The last step includes an oxidative coupling with phenols. The analogous CH compounds of general formula (IV), in which $R_1$ is the radical:

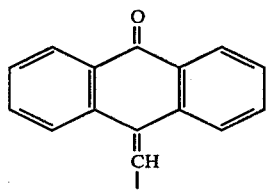

can be prepared from the corresponding aldehydes, in which $R_1$ is —CHO, which can be obtained, for example, via a Vilsmeier reaction.

Furthermore, stilbenes and merocyanines and possibly aza analogues of general formula (IV) are suitable, wherein n is, for example, 1 and $R_1$ is, for example, one of the following radicals:

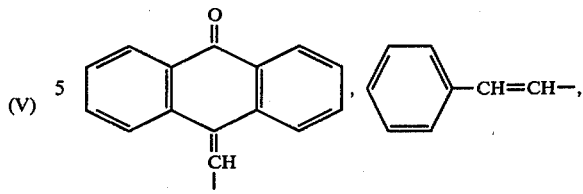

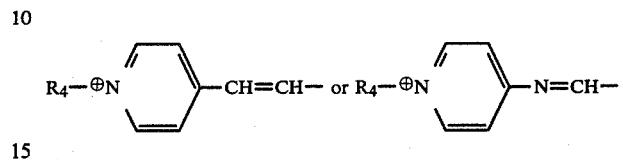

$R_4$ being an alkyl radical containing, for example, up to 5 carbon atoms and preferably being a methyl or ethyl radical. The attachment of dyestuffs in the above manner to cryptand systems leads to the achievement of a comparatively high complex stability, especially in an aqueous medium, and to a comparatively high selectivity. In this case, it is especially advantageous to couple reactive diazonium salts with benzocryptades of the general formula:

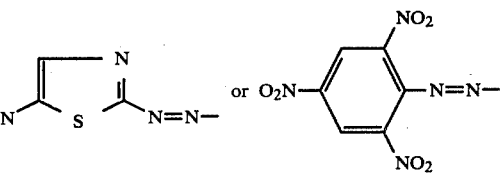

wherein $R_2$ can be, for example, a radical of the formula:

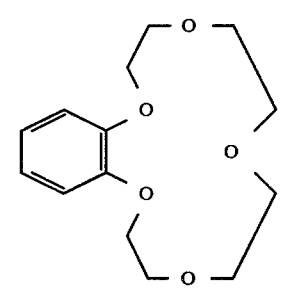

Benzocrown ethers of the general formula:

(VII)

have proved to be model substances for the synthesis which also give conclusions regarding the behavior to be expected with regard to ions. The variation of the hollow space size requires benzocryptands, such as are needed for compounds of general formula (VI), but which, however, are shortened or lengthened by one or more oxyethylene units.

Furthermore, cryptands of the following type:

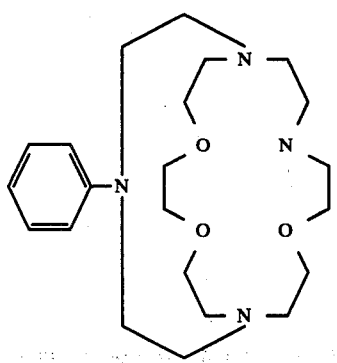

(VIII)

are also suitable.

In a similar manner, there can also be prepared those of the following type:

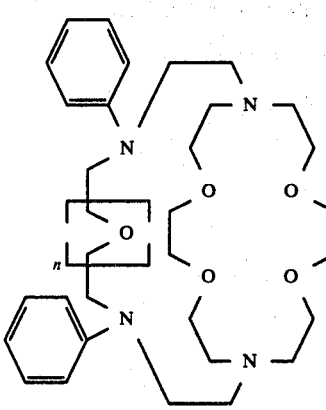

(IX)

which, similarly to the simple phenylaza-crown ethers, can, by reaction in the 4-position of the aniline moiety, be reacted to give dyestuff cryptands of, for example, the following general formulae:

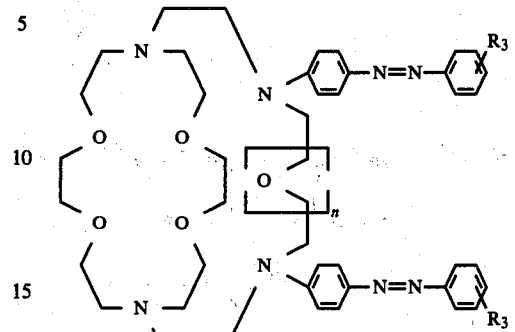

(IXa)

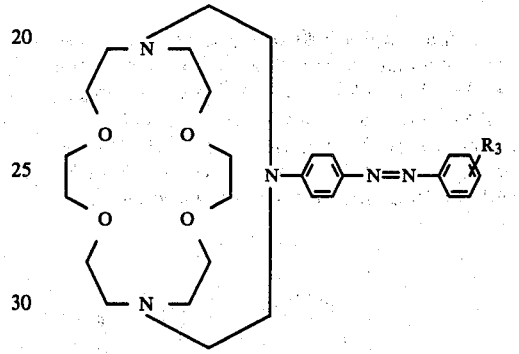

(IXb)

wherein $R_3$ is a nitro, cyano, sulphonium or like group.

Besides the previously mentioned types, in which a mesomery influencing takes place, for example, by a disturbance due to incorporated ions on a hetero atom, an attack can also take place on the antiauxochrome or on an azo bridge according to the following general formulae:

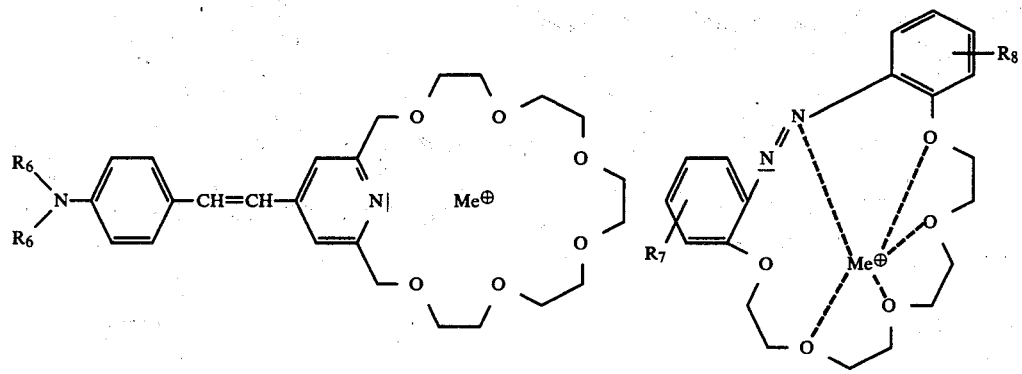

(X)

wherein $R_6$ is a lower alkyl group which can possibly also be cyclic and $R_7$ and $R_8$, which can be the same or different, are hydrogen atoms or nitro, cyano or dialkylamino groups.

Examples of fluorescent dyestuff crown ethers are those of the formula:

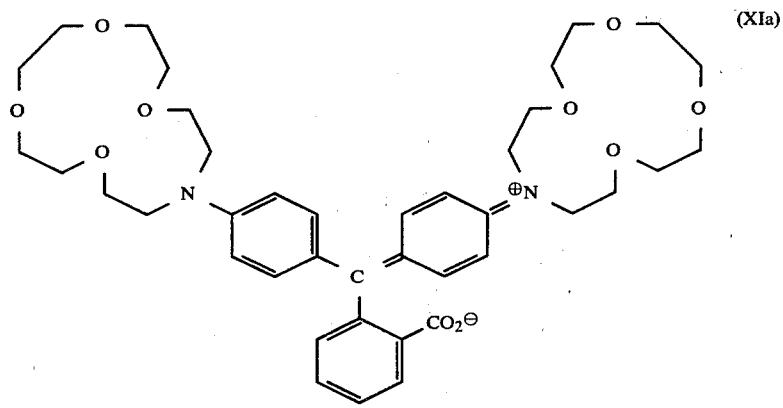

Further examples of dyestuff crown ethers are those of the general formula (XIb) (wherein X is a nitrogen atom or —CH=; Y is —CH$_2$—, —NH— or an oxygen or sulphur atom and n is 1, 2 or 3), such as methylene blue; crown ethers of the general formulae (XIc) and (XId) (azomethine dyestuff crown ethers), wherein R$_9$ is a lower alkyl radical and A$^\ominus$ is a conventional anion; crown ethers of the formula (XIe) (anthracilin crown ethers), crown ethers of the formula (XIf) (alizarin crown ethers) and crown ethers of the formula (XIg) (cyanine type). An example of a lipophilic hollow space is the compound of general formula (XII), in which n is a whole number of from 1 to 6 and R$_{10}$ is a hydrogen atom or a lower alkyl or aryl radical.

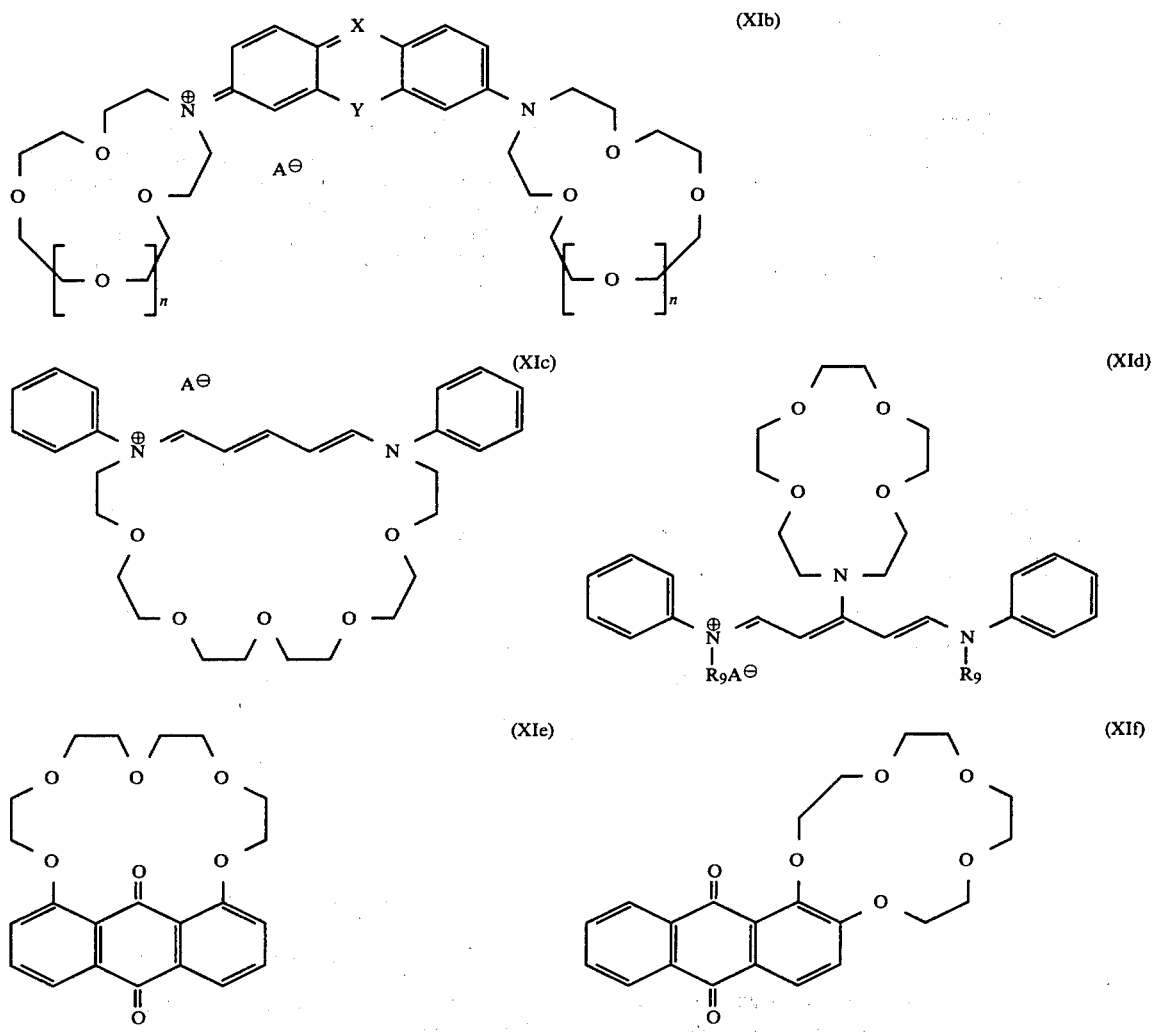

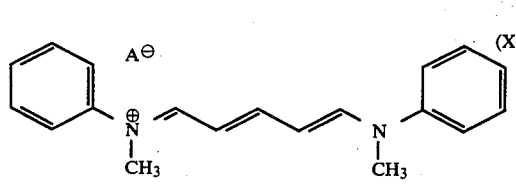 (XIg)

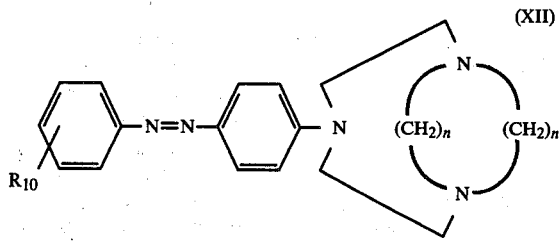 (XII)

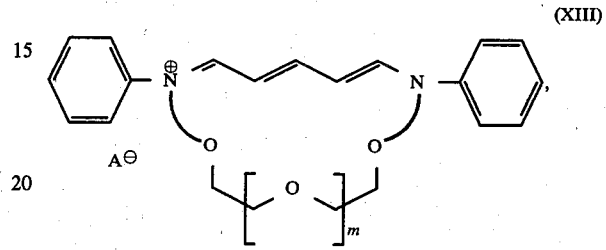 (XIII)

wherein m is 1, 2 or 3 and $A^{\ominus}$ is an anion.

As fluorescent dyestuffs, those of the phthalein group (general formula (XIa)) are especially preferred, the crown ether rings thereby being applied to the chromophore at the places which are especially sensitively influenced in the case of complexing. In the case of such fluorescent dyestuffs, a stronger disturbance of the color or of the fluorescence (phosphorescence) of the chromophore is present due to the complexing. By adjustment of the crown ether hollow space to certain ions, such exchange actions and effects can be selectively adjusted to certain kinds of ions. Apart from the alkali metal and alkaline earth metal ions, the heavy metal ions, as well as ammonium ions and other organic onium ions, such as the phosphonium ions, play a part. Thus, for example, in this case ammonium group-containing disinfection agents can be detected.

By the introduction of dyestuff crown ethers (or, vice versa, of ions) into fibers or synthetic resin films or the like, by means of a dyeing process, which can correspond to mordanting, not only can dyestuffs be fixed on to textiles and the like but also modified dyeing processes and color nuances can be achieved. The binding is thereby not ionic and not covalent but rather takes place via a crown ether-host-guest reciprocal action, i.e. ion-dipole reciprocal action; it can be made reversible and thus can be analytically evaluated.

In particular, use can also be made of anthraquinones with functional groups, such as sulphonic acid groups, or of naphthoquinone-sulphonic acids which have previously been used or are even today still used in dyeing. According to the present invention, they can be ion-selectively modified and thus serve for the detection of particular ions. They can also be applied or bound to paper or fibers, as well as to polymers.

In the case of all dyestuffs and especially also the cyanine dyestuffs, reference is made to the appropriate organic chemical textbooks and dyestuff reference books. A very suitable cyanine dyestuff is König's salt (formula (XIg)) which can easily be prepared from pyridine and N-methylaniline.

König's salt can be modified by the attachment of crown ethers in such a manner that, in the case of complex formation with alkali metal or alkaline earth metal or heavy metal ions, color changes or color effects occur which can be used for the detection or concentration determination of these ions, even in the case of the simultaneous presence of other ions.

One possibility for the modification of cyanine dyestuffs of the König's salt type consists in the bridging of the two nitrogen centers by a crown ether-like cyclic or open-chained crown ether unit with donor groups according to the following general formula:

In this way, the chromophore is additionally disturbed in the case of the host-guest reciprocal action, i.e. in the case of nesting in of the cation, due to the positive charge of the cation. Due to the crown ether structure attached directly on to the sensitive part (electron cloud) of the chromophore, the cation is attracted and fixed and is able to change this chromophore system by the attraction of electrons from the loose $\pi$-electron cloud, which brings about the color effect. By means of shorter or longer crown ether bridges, which can be modified by various hetero atoms or by the incorporation of rigid aromatic structural elements, such as pyridine rings or the like, these dyestuffs can be influenced in the desired manner in the case of the complexing.

Another possibility of preparing crown ethers with a cyanine structure of the König's salt type consists in starting from the aniline provided in the p-position with an aza crown ether ring and, in the case of the complexing of the lone electron pair on the p-amino nitrogen of the crown ether ring, sensitively to disturb by the nesting in of the ion so that this lone electron pair is only available to a limited extent for mesomerism, which forces a color change.

The present invention also includes the use of complex ligands in the form of a cyclic peptide or of a peptide which, in the presence of the ion or of the polar substance, assumes the necessary secondary, tertiary or quaternary structure. Thus, for example, natural ionophores, such as valinomycin, nonactin, gramacidin and similar peptides, can also be employed for the ion-selective color reactions or color tests according to the present invention. In this case, the procedure can be as follows: into valinomycin there is incorporated a dyestuff salt, for example, 2,4-dinitrophenylhydrazonium chloride, sodium picrate or a similar dyestuff. The valinomycin-dyestuff complex generally has a different color or absorption maximum from that of the free dyestuff. In a second step, to this valinomycin-dyestuff complex there is added the salt solution, the concentration of which is to be tested, the potassium-specific valinomycin thereby complexing the potassium ions present in the solution, the dyestuff being forced out of the valinomycin hollow spaces and another color or absorption spectrum now again being displayed in the solution.

In this way, the potassium specificity of valinomycin can be utilized for color tests. As a simple dyestuff system which can be used for incorporation into or adding on to valinomycin and subsequent expulsion with potassium ions, there can be used, in particular, hydrzinium salts with various attached mesomeric systems, for example azo functions. Dyestuff cations are used which are sterically as little demanding as possible and which form with valinomycin a weak but still sufficiently stable complex which must also not be too strong so that it can thereafter again be quantitatively broken down with potassium ions, even in low concentration.

Analogous experiments with crown ethers, such as the crown ether [18] crown-6, which thus have a structure which is comparable with that of valinomycin and nonactin, permits the recognition of marked color effects or changes of the long wavelength absorption of the dyestuff in the state of being bound on to the crown ether and in the free state. The use not only of cationic dyestuff salts, for example 2,4-dinitrophenylhydrazonium ions, as well as of anionic color carriers, for example picrate ions, offer a plenitude of variations and application possibilities, the choice of which can be exactly "tailored" from case to case, i.e. to the components employed.

Another dyestuff which is preferred is the azo compound of the formula:

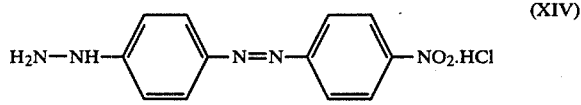

(XIV)

As examples of neutral guest molecules which, according to the present invention, can be selectively detected, there may be mentioned, in particular, urea, thiourea, ammonium salts, such as choline, guanine, guanidine, uric acid, creatinine, amino acids and sugars, namely, according to the present invention, on the basis of their color effects, not only qualitatively but also quantitatively. For the quantitative determination of urea in aqueous solutions, a quinoline ligand can be synthesized which can be used not only for urea but also for thiourea (see Tetrahedron Letters, 3, 309–312/1973).

The process according to the present invention with the use of the novel dyestuff systems is of great interest since it readily permits a plenitude of measurements and calculations which extend, for example, to the ion selectivity, caused by the complex constants with regard to various ions and the influence of ions of particular charge density on the chromophore system of the most varied types of dyestuffs with regard to extinction and absorption properties. In many cases, preliminary calculations with molecule orbital methods are possible.

Another structural variant of intramolecular ionophore/chromophore combination of the (XV) or (XVI) type is shown by another kind of possibility of influencing selectivity: the cations fixed in the crown ether hollow space are additionally co-ordinated by the donor center present on a comparatively short or comparatively long side chain, which can be a phenolic or $CH_2O^\ominus$ group or $COO^\ominus$ or $SO_3^\ominus$. Two influences are here combined: the negative charge of the side chain bonds the cation electrostatically more strongly than would be possible by a crown ether ring because of the ion-dipole reciprocal action. However, the cation must, nevertheless, pass into the crown ether ring, i.e. it is there tested and selected for its size. Overall, higher complex constants are experimentally observed on the basis of the stronger bonding of the cation to the ligands, a higher selectivity of the cation embedded in the crown ether ring, as well as, as a result thereof, a strong influencing of the chromophore system because of the favorable position of the equilibrium in comparison with the previously described ligands and a special selectivity towards cations with high charge density, for example calcium ions. Such ligand systems, when optimized for certain cations, can possibly be used for the specific differentiation of simple/plural charged cations:

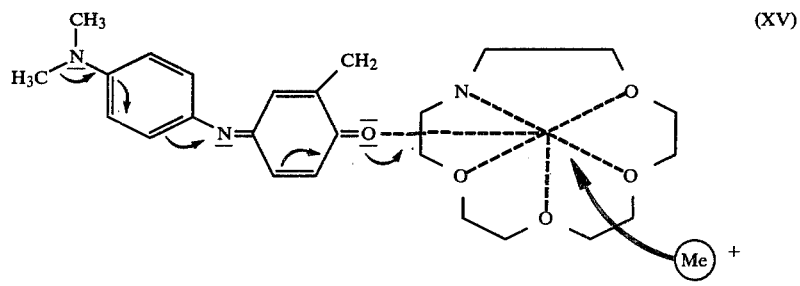

(XV)

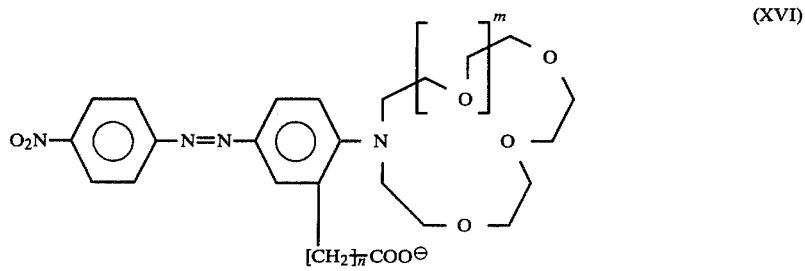

(XVI)

-continued

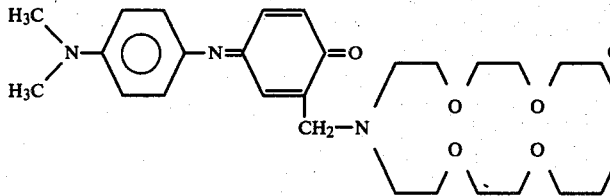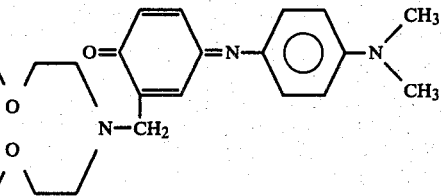

The process according to the present invention provides a series of novel and practical uses:

(a) With the help of the crown ether dyestuffs, indicators and probes can be developed, for example for the detection of the phase transfer of salts, for the study of ion transport by lipophilic media, for example synthetic and biological membranes, i.e. for investigations in connection with membranological research from a physiological or pathological point of view.

(b) Another use is the possibility of ion-selectively coloring tissue sections. A possibly quantitative evaluation hereby permits conclusions regarding the nature and concentration of ions which are made visible by the displacement of $\lambda_{max}$ and extinction.

(c) The use of chromophore cryptand systems ensures, especially in aqueous media, not only a substantially higher complex stability but also an improved selectivity. Besides the qualitative and quantitative photometric detection of the alkali metals and alkaline earth metals, as well as of the ammonium ions, with the help of host chromophores of various hollow space size in solutions, for example in blood or sera and other body fluids, these can also be identified on carrier materials. The use as spray reagents for ion chromatograms or silicone prints in the field of medical diagnosis is thereby possible. In the manner of thermography, either by spraying areas of tissue or their imprints with ion-selective dyestuffs and fluorescent dyestuffs, physiological or pathological salt concentrations can be made visible. From this there follows the possibility of differentiating diseased areas, for example cancerous tissue, from healthy material.

(d) From the knowledge of the complexing of organic ammonium and guanidinium salts, as well as of neutral molecules, for example urea and CH-acid compounds, it is, according to the present invention, now possible to carry out detection with appropriate host chromophores. The usefulness from a medicinal or biochemical point of view hereby lies in the specific photometric detection of certain substances which are peculiar to the body and the kinetic monitoring of enzymatic processes. Having regard thereto, there can be considered the attachment of lipophilic hollow spaces in the form of endolipophilic or endohydrophobic macrocyclic compounds with exohydrophilic or exopolarophilic molecular peripheries on sensitive i.e. chromophore-influencing, positions of one of the dyestuffs which permit the enveloping of an appropriate neutral particle and, probably due to hydrogen bridges, bring about a change of the absorption or extinction.

The following Examples are given for the purpose of illustrating the present invention:

EXAMPLE 1

Photometric determination of potassium with an ion-selective dyestuff which contains the chromophore covalently bound via a mesomeric system.

An ion-selective dyestuff of general formula (IV') (n=1) is dissolved in chloroform and shaken up with a solution which contains potassium ions. The dyestuff complexed with potassium passes over into the aqueous phase and can be determined quantitatively at 600 nm in a photometer, depending upon the activity of the potassium ions present.

The dyestuff (5-nitro-1,3-thiazole-2-azo-[3-(12-hydroxy-1,4,7,10-tetraoxadodecyl]-4-hydroxybenzene) can be prepared by reacting 2-amino-5-nitrothiazole in 85% phosphoric acid with sodium nitrite and subsequently adding benzo[15] crown-5. The intensively red suspension is mixed with water and extracted with chloroform. After drying with anhydrous sodium sulphate and removing the solvent in a vacuum, it is separated by column chromatography on silica gel. With the use of chloroform, there is first obtained the ring-closed dyestuff 5-nitro-1,3-thiazole-2-azo[1,4,7,10,13-pentaoxa[13](3,4)benzophane (VII)]. By the addition of 5% ethanol to the eluent, there is obtained the ring-open dyestuff (IV') (n=1). Both dyestuffs can be obtained in crystalline form by dissolving in ethyl acetate and adding petroleum ether (b.p. 60°-90° C.). The melting points are 169°-171° C. (VII) and 112°-115° C. (IV').

EXAMPLE 2

For the investigation of the properties of the ion-selective dyestuffs mentioned in Example 1 for test strips, a solution of the dyestuff is applied dropwise to a strip of filter paper and the strip then dried. The paper strip treated in this manner becomes a deep red color upon the application thereto of sample solutions which contain potassium ions. Besides this qualitative method of detection, the colored strip can also be quantitatively evaluated in a reflection photometer.

EXAMPLE 3

Selective photometric determination of potassium with a ligand which carries a covalently-bound chromophore.

A compound of general formula (IV), in which n is 1 and $R_1$ is the radical:

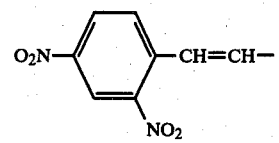

is obtained by reacting 2,4-dinitrotoluene for 3 hours with N-(p-formylphenyl)-aza[15] crown-5 and a few drops of piperidine at 100° C. The solidified melt is dissolved in a little ethyl acetate, filtered and the filtrate evaporated in a vacuum. The residue is purified by column chromatography on silica gel, using ethyl acetate/5-10% ethanol. Upon concentrating the eluate, 2,4-dinitro-4'-(4,7,10,13-tetraoxa-1-azocyclopentadec-1-yl)-stilbene crystallizes out; m.p. 143°-146° C.

7.5 mg. Dyestuff are dissolved in 250 ml. methanol. Furthermore, 0.1 M solutions are prepared of calcium chloride, sodium chloride, potassium chloride, lithium chloride and magnesium chloride, in each case in 0.1 M triethanolamine hydrochloride/sodium hydroxide buffer (pH 7.0).

There is also prepared a series of solutions with 0.001 to 0.1 M potassium chloride, again in each case in 0.1 M triethanolamine hydrochloride/sodium hydroxide buffer (pH 7.0).

3 ml. amounts of dyestuff solution are mixed with 0.5 ml. of the particular salt solution to be investigated and the absorption behavior determined in a photometer at 366 nm. This dyestuff shows a spectrum towards potassium which is different from that in the presence of lithium, sodium, calcium, barium and magnesium. The concentration of the potassium ions is directly proportional to the extinction. The absorption spectra of some of these metal ions are given in FIG. 1 of the accompanying drawings.

EXAMPLE 4

Photometric determination of calcium and lithium with a heterocyclic crown ether of formula (IV) in which n is 1 and $R_1$ is

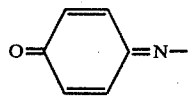

and thus the chromophore is covalently attached.

1,4-Benzoquinone-(4,7,10,13-tetraoxa-1-azacyclopentadec-1-yl)-phenylimine is obtained by the oxidative coupling of N-(4-aminophenyl)-aza[15] crown-5 with phenol. Furthermore, silver nitrate is reacted with sodium chloride and some starch, sodium carbonate and phenol are added thereto and a solution of N-(4-aminophenyl)-aza[15]-crown-5 in concentrated hydrochloric acid added thereto dropwise. After the reaction, the reaction mixture is stirred with ethyl acetate, dried with anhydrous sodium sulphate and evaporated in a vacuum. The residue crystallizes from tetrahydrofuran with diethyl ether at 0° C.; m.p. 55°–56° C.; $\lambda_{max}=583$, log $\epsilon=4.77$.

The dyestuff is dissolved in chloroform ($E_{578\ nm}=0.8$) and mixed with an equal amount by volume of an aqueous salt solution. With lithium and calcium, a color change was measured at 578 nm which is directly proportional to the ions to be determined.

By the oxidative coupling of α-naphthol with N-(4-aminophenyl)-aza[15]-crown-5, there is obtained 1,4-naphthquinone-4-(4,7,10,13-tetraoxa-1-azacyclopentadec-1-yl)-phenylamine; m.p. 124°–125° C.; $\lambda_{max}=577$, log $\epsilon=4.41$. The color displacement by metal ions corresponds to that of the benzoquinone derivative.

EXAMPLE 5

Orange-colored 2,4-dinitrophenylhydrazinium hydrochloride ($\lambda_{max}$ 395 nm) is dissolved in methanol/water and mixed with molar amounts of crown ether [18] crown-6. A change of the absorption (brightening) is observed between the free dyestuff and the dyestuff bound in the ionophore complex ($\lambda_{max} \approx 384$ nm). To this is added an aqueous methanolic solution containing potassium or sodium ions, for example a solution of sodium perchlorate or potassium thiocyanate, a deepening of the color being observed since the liberated dyestuff again displays the initial absorption maximum.

If the crown ether in the above Example is replaced by another ionophore, such as valinomycin or nonactin, then, depending upon the ionophore, more or less strongly marked color effects or absorption changes are observed.

EXAMPLE 6

Figure 2:
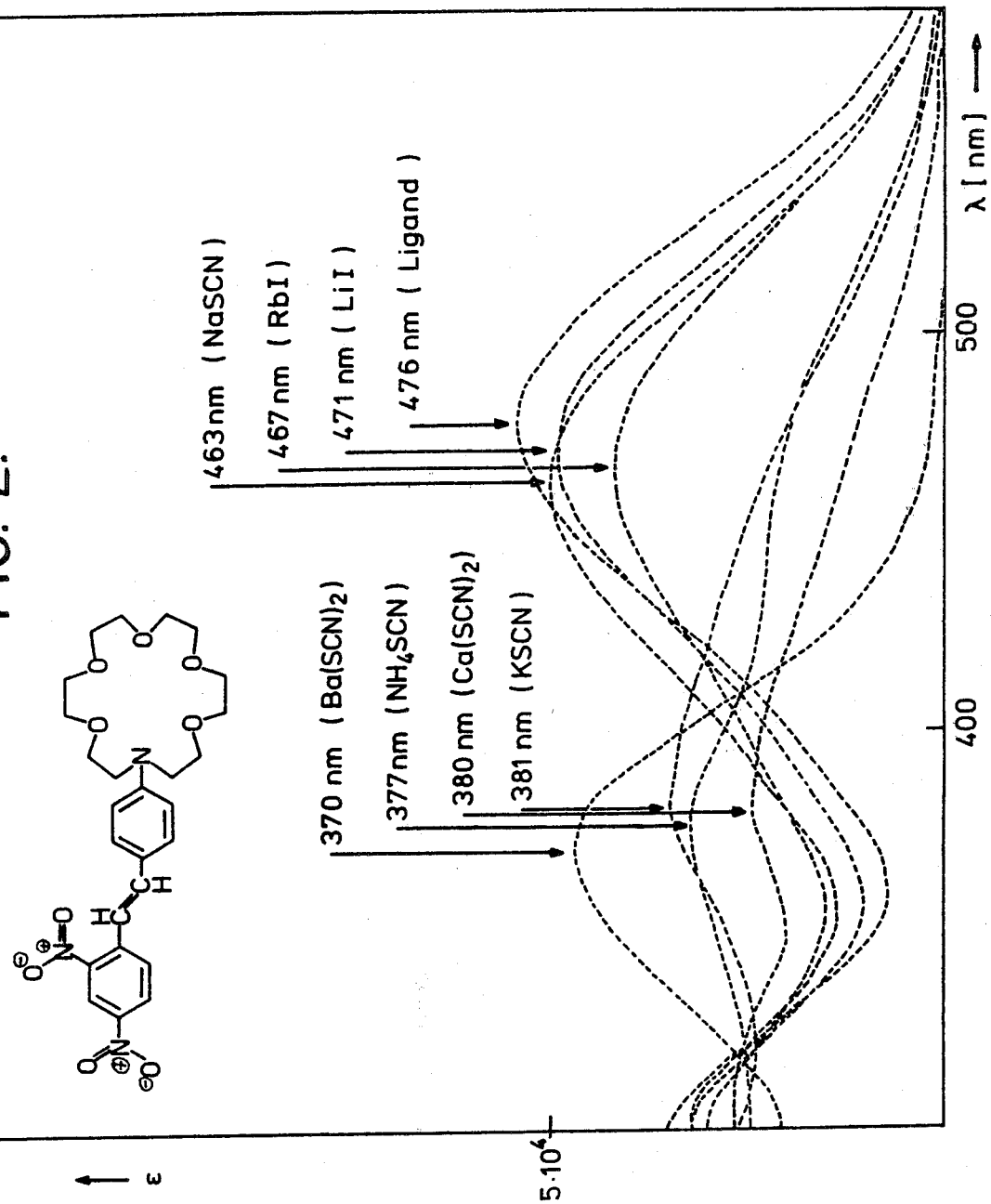

In a manner analogous to that described in Example 3, 2,4-dinitrotoluene is heated with N-(p-formylphenyl)-aza[18]-crown-6 and a few drops of piperidine for 4 to 5 hours at 100°–110° C. The reaction mixture is dissolved in dichloromethane and chromatographed on silica gel with ethyl acetate/chloroform (1:1 v/v). After recrystallization from ethyl acetate/ethanol (1:1 v/v), there is obtained the dyestuff 2,4-dinitro-4'-(4,7,10,13,16-pentaoxa-1-azacyclooctadec-1-yl)-stilbene; m.p. 90°–91° C. The absorption spectra of the dyestuff and of its complexes with barium, ammonium, calcium, potassium, sodium, rubidium and lithium ions are given in FIG. 2 of the accompanying drawings.

EXAMPLE 7

Figure 3:
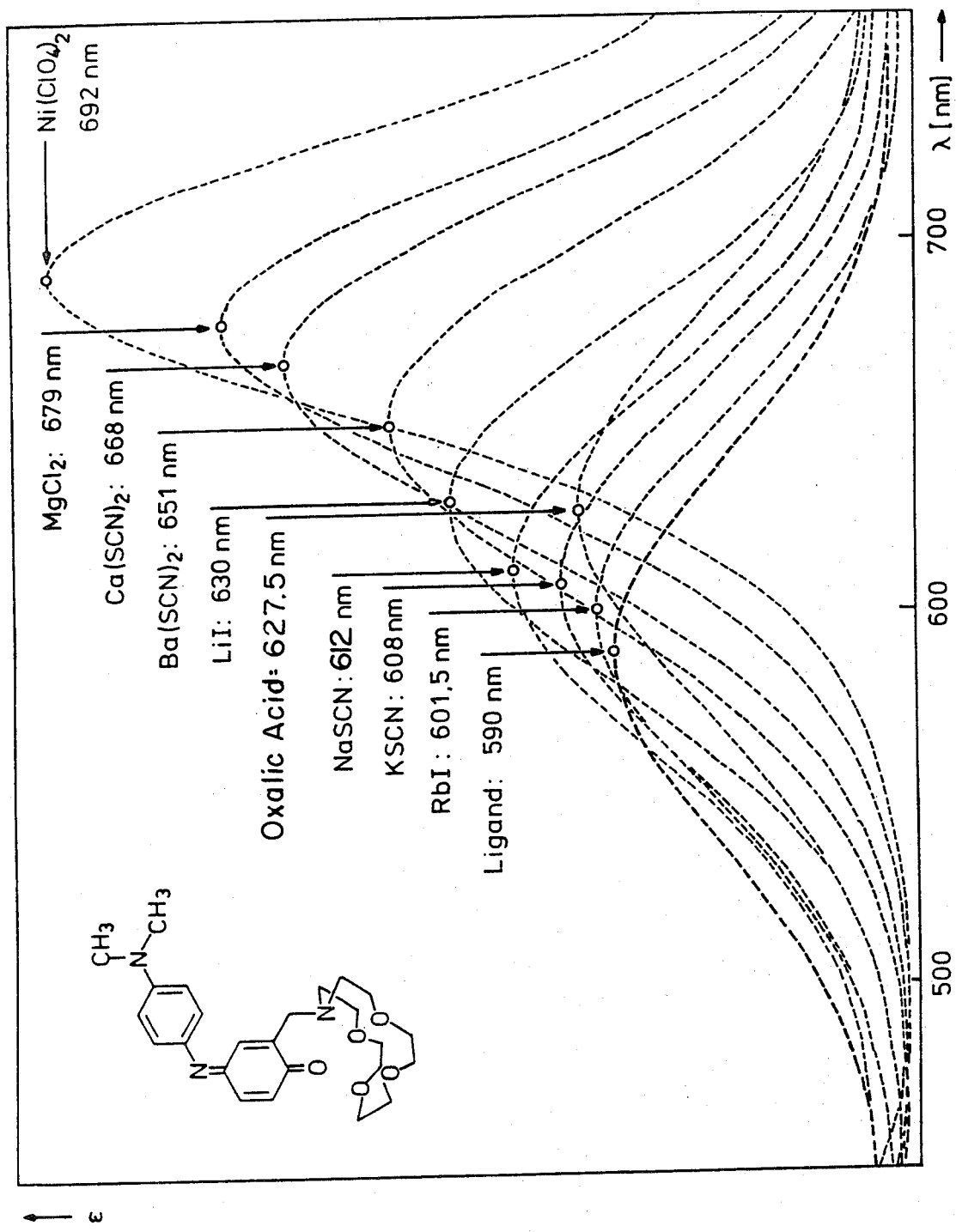

In a manner analogous to that described in Example 4, by the oxidative coupling of N-(2-hydroxybenzyl)-monoaza[15]crown-5 with 4-amino-N,N-dimethylaniline, there is obtained a blue dyestuff which can be extracted with ethyl acetate. After drying the extract with anhydrous magnesium sulphate, filtering and evaporating the filtrate in a vacuum, the residue obtained is chromatographed on silica gel with ethanol/ethyl acetate (1:9 v/v). The absorption spectra of the dyestuff and of its complexes with sodium, potassium, rubidium, magnesium, calcium, barium, lithium and nickel ions are given in FIG. 3 of the accompanying drawings.

EXAMPLE 8

Figure 4:
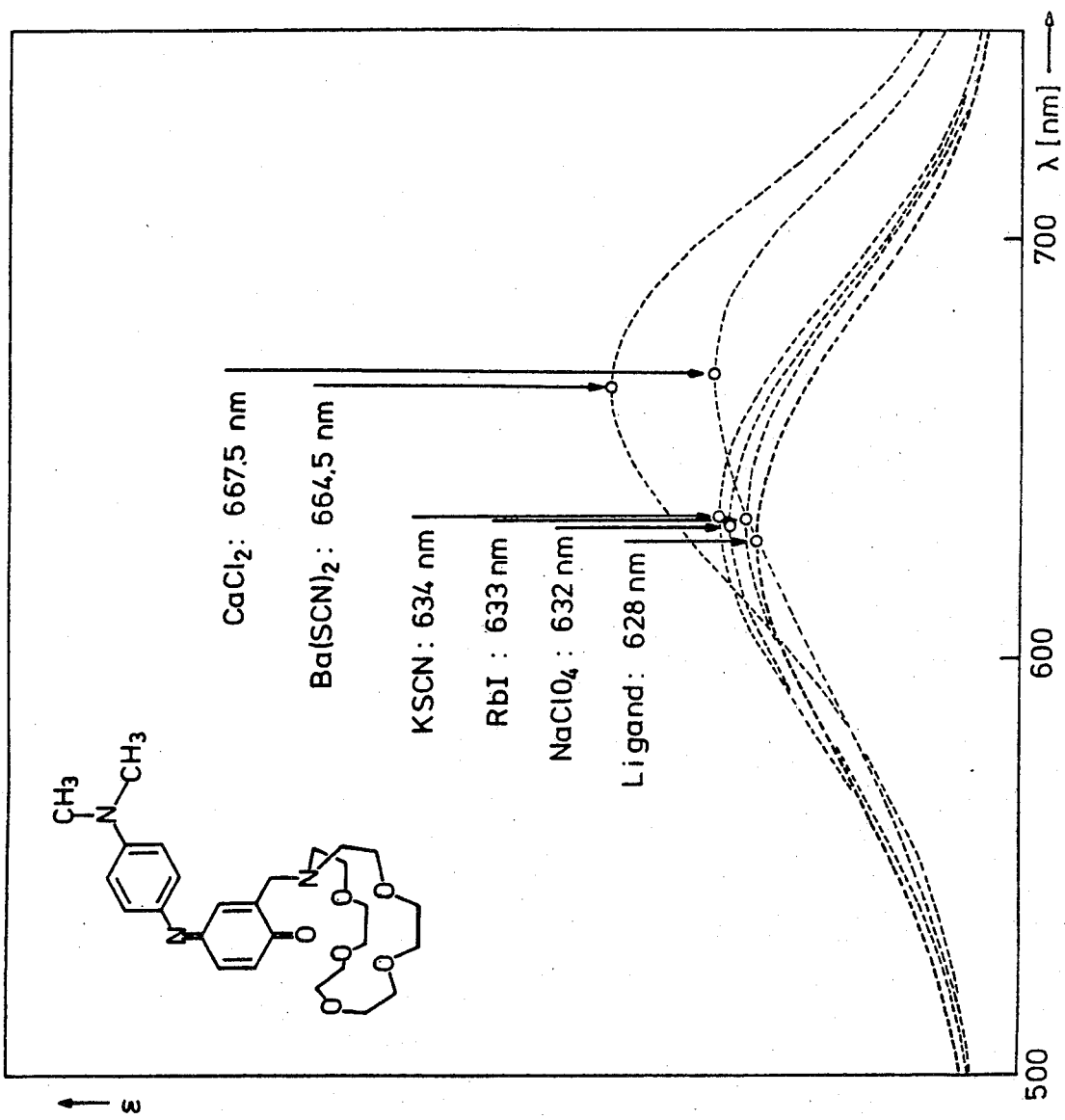

In a manner analogous to that described in Example 7, from N-(2-hydroxybenzyl)-monoaza[18]crown-6, there is obtained a dyestuff, the absorption spectra of the free and complexed state of which are given in FIG. 4 of the accompanying drawings.

EXAMPLE 9

Figure 5:
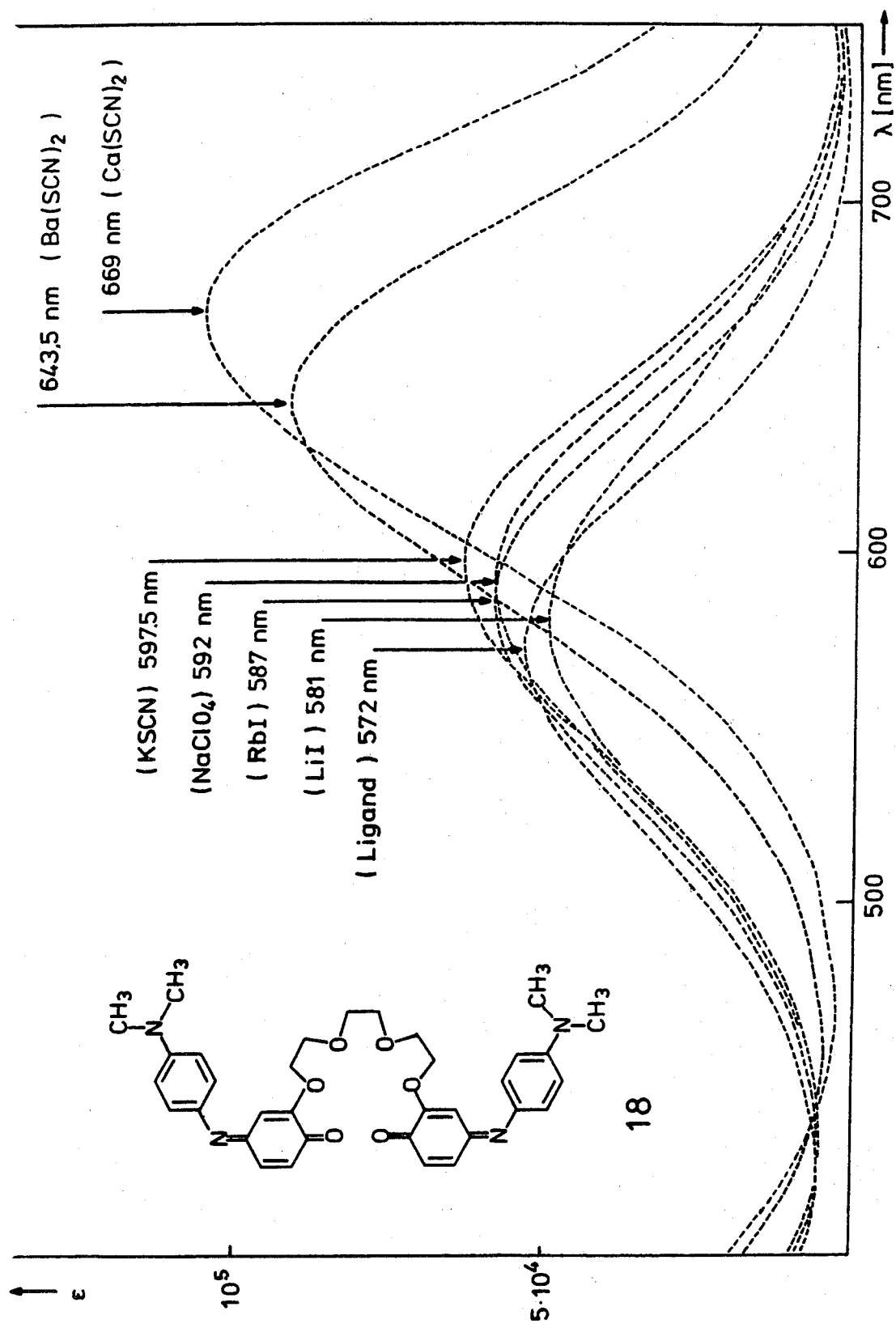

The spectra of 1,8-bis-[1-(4-dimethylaminophenylimino)-p-benzoquin-3-oxy]-3,6-dioxaoctane in the free form and in the complexed forms with potassium, sodium, lithium, rubidium, barium and calcium ions are given in FIG. 5 of the accompanying drawings. This compound can be prepared by reducing p-nitroso-N,N-dimethylaniline with hydrochloric acid and zinc dust and reacting with 1,8-bis-(2-hydroxyphenoxy)-3,8-dioxaoctane in the presence of sodium hydroxide and potassium dichromate. Upon acidification with glacial acetic acid, the blue dyestuff precipitates out. After drying out with acetone, it is cooled, filtered off with suction and washed with a little acetone. It is then extracted with acetone in a hot extractor and chromatographed on silica gel with ethyl acetate. The dyestuff is obtained by adding 5% ethanol to the ethyl acetate solution. After crystallization from acetone/n-heptane, the dyestuff melts at 112°–115° C.; $\lambda_{max}=572$ log $\epsilon=4.73$.

EXAMPLE 10

The spectrum of the dyestuff (IV), in which $R_1$ is

Figure 6:
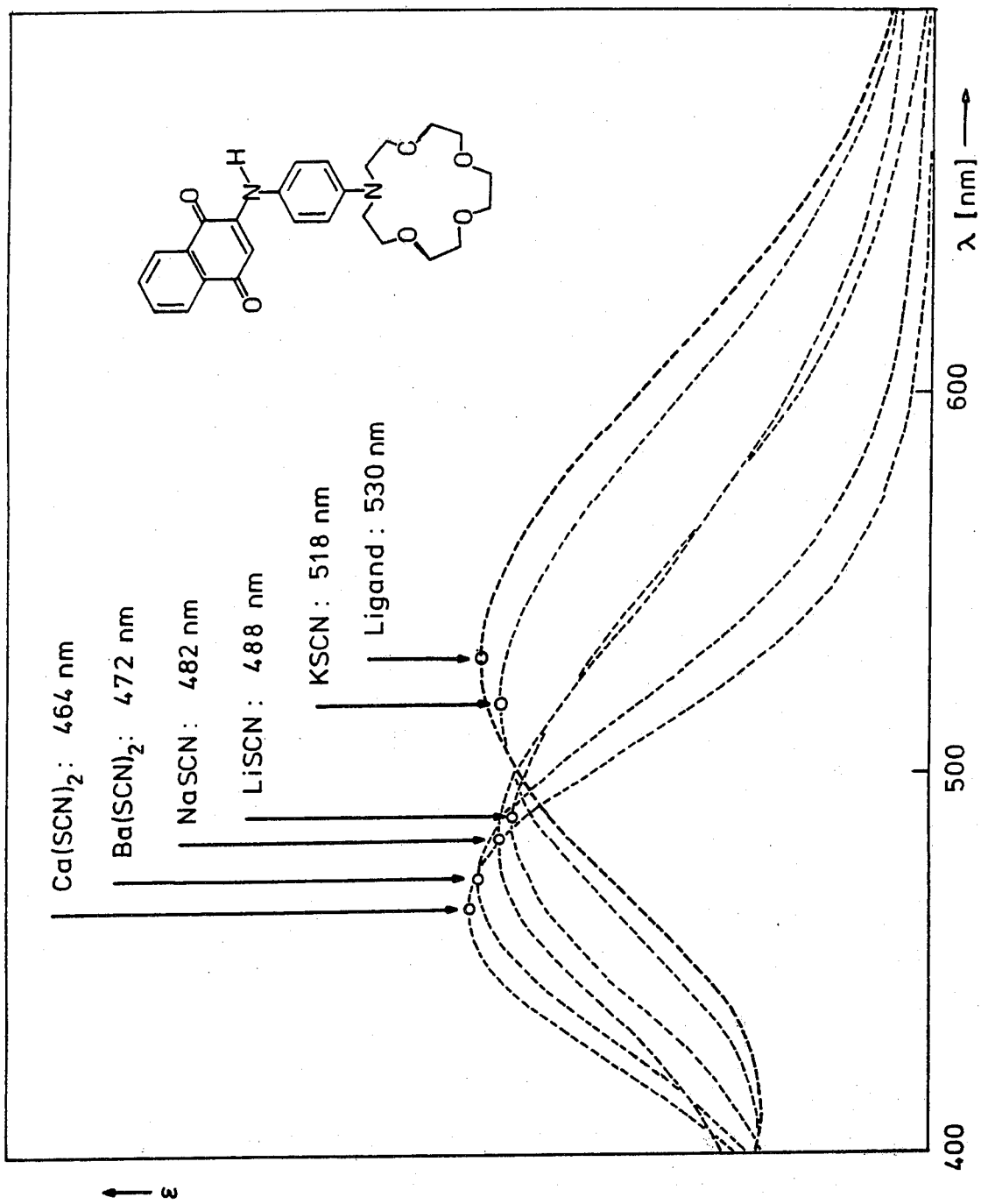

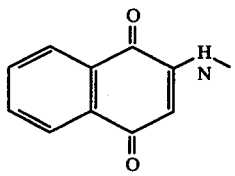

and n is 1, as well as the spectra of the metal ion complexes with calcium, barium, sodium, lithium and potassium, are given in FIG. 6 of the accompanying drawings. This dyestuff is obtained by suspending N-(4-aminophenyl)-aza[15]-crown-5 and 1,4-naphthoquinone with copper acetate monohydrate in ethanol, boiling for 1 hour and passing through air. After removing the solvent in a vacuum, the residue is mixed with water, extracted with dichloromethane, dried with anhydrous magnesium sulphate and evaporated in a vacuum. The oily residue is purified on silica gel with dichloromethane. The eluate initially contains excess naphthoquinone and, after the addition of 5% ethanol, contains the desired dyestuff, which can be recrystallized from ethyl acetate.

It will be understood that the specification and examples are illustrative, but not limitative of the present invention and that other embodiments within the spirit and scope of the invention will suggest themselves to those skilled in the art.

What is claimed is:

1. Method for the determination of a component in a liquid which component is selected from ions, polar substances and lipophilic substances, which method comprises contacting a liquid sample containing said component with, and allowing same to act upon, a complex ligand or hose molecule which is selective toward the component, and being selected from the group consisting of a cyclodextrin, a cyclophane, a crown ether or derivative thereof, a cryptand or derivative thereof, a podand or derivative thereof, a valinomycin, a gramacidin and a nonactin said complex ligand or host molecule being bonded to a chromophore material, and measuring the change of extinction or the wavelength displacement of the resulting mixture as a measure of the initial content of said component.

2. Method as claimed in claim 1 wherein said component is a polar substance.

3. Method as claimed in claim 1 wherein said component is a lipophilic substance.

4. Method as claimed in claim 1 wherein said component is a mixture of polar and lipophilic substances.

5. Method as claimed in claim 1 wherein said chromophore material is in the form of an inclusion complex.

6. Method as claimed in claim 1 wherein said host molecule is a cyclodextrin.

7. Method as claimed in claim 1 wherein said host molecule is a cyclophane.

8. Method as claimed in claim 1 wherein said selective complex ligand is a crown ether or derivative thereof.

9. Method as claimed in claim 1 wherein said selective complex ligand is a cryptand or derivative thereof.

10. Method as claimed in claim 1 wherein said selective complex ligand is a podand or derivative thereof.

11. Method as claimed in claim 1 wherein said component is constituted by ions in said liquid.

12. Method as claimed in claim 11 wherein said component is an anion.

13. Method as claimed in claim 12 wherein said anion is a chloride, bromide, iodide, sulfate, nitrate, nitrite, phosphate, diphosphate, triphosphate, hydrogen phosphate or hydrogen carbonate ion.

14. Method as claimed in claim 11 wherein said component is an cation.

15. Method as claimed in claim 14 wherein said cation is an ammonium, alkali metal, alkaline earth metal or other metal ion.

16. Method as claimed in claim 15 wherein said cation is a lithium, sodium, potassium, magnesium or calcium ion or an iron, zinc, copper, cobalt, nickel, molybdenum or chromium ion.

17. Method as claimed in claim 1 wherein said complex ligand is a valinomycin, a gramacidin or a nonactin.

18. Method as claimed in claim 1 wherein said component is a polar substance selected from the group consisting of urea, thiourea, guanidine, uric acid, choline, creatinine, amino acids and sugars.

19. Method as claimed in claim 1 wherein said chromophore is linked to several identical or different complex ligands or host molecules.

20. Method as claimed in claim 1 wherein said complex ligand or host molecule is linked to several identical or different chromophores.

21. Method as claimed in claim 1 wherein said complex ligand or host molecule is bonded to the chromophore via a direct covalent bond.

22. Method as claimed in claim 1 wherein said complex ligand or host molecule is bonded to the chromophore via a heteropolar bond.

23. Method as claimed in claim 1 wherein said complex ligand or host molecule is bonded to the chromophore via a hydrophobic bond.

24. Method as claimed in claim 1 wherein said complex ligand or host molecule is bonded to the chromophore via a hydrogen bridge.

25. Method as claimed in claim 1 wherein said component is a lipophilic substance selected from the group consisting of steroids and lipids.

26. Method as claimed in claim 25 wherein said lipophilic substance is cholesterol, triglyceride or lecithin.

27. Method as claimed in claim 1 wherein said complex ligand or host molecule is applied to or incorporated into a solid carrier.

28. Method as claimed in claim 27 wherein said carrier is paper, synthetic resin film, glass, aluminum oxide, silicon oxide, natural or synthetic fibers or metal.

29. Method as claimed in claim 1 wherein said chromophore is a dyestuff or a chromogen having an absorption spectrum which is changed by reciprocal action with said component, by charge displacement or disturbance of the mesomeric system.

30. Method as claimed in claim 29 wherein said chromophore is selected from materials having a polyene, meriquinoid, quinone, azo, pyrrole, merocyanin, indigo, indophenol, stilbene, azomethine, anthraquinone, naphthoquinone, cyanine, phthalein, polymethine or alizarine structure.

31. Method as claimed in claim 29 wherein said dyestuff contains a carboxylate, sulfonate, phenolate or thiophenolate grouping.

32. Method as claimed in claim 29 wherein said chromophore is an acidic dyestuff thereof.

33. Method as claimed in claim 32 wherein said chromophore is a salt of an acidic dyestuff selected from lithium, sodium, potassium, ammonium, calcium, alkylammonium or magnesium salts.

* * * * *

UNITED STATES PATENT AND TRADEMARK OFFICE
CERTIFICATE OF CORRECTION

PATENT NO. : 4,367,072
DATED : January 4, 1983
INVENTOR(S) : Freidrich Vogtles et al It is certified that error appears in the above-identified patent and that said Letters Patent is hereby corrected as shown below:

Claim 1, line 6, "hose" should read -- host --.
Claim 32, line 2, after "dyestuff" insert -- or salt --.

Signed and Sealed this

Twentieth Day of November 1984

[SEAL]

Attest:

GERALD J. MOSSINGHOFF

Attesting Officer    Commissioner of Patents and Trademarks